United States Patent [19]

Stevens

[11] 4,074,051
[45] Feb. 14, 1978

[54] 3-PYRAZOLIDINONE DERIVATIVES

[75] Inventor: John Stevens, Harlow, England

[73] Assignee: Minnesota Mining and Manufacturing Company, St. Paul, Minn.

[21] Appl. No.: 420,292

[22] Filed: Nov. 29, 1973

Related U.S. Application Data

[63] Continuation-in-part of Ser. No. 206,168, Dec. 8, 1971, abandoned, which is a continuation of Ser. No. 853,941, Aug. 8, 1969, abandoned.

[51] Int. Cl.$^2$ .......................................... C07D 231/08
[52] U.S. Cl. .................................. 544/140; 544/171; 548/362; 548/363; 560/172; 260/293.51; 260/293.7; 260/293.88; 260/465.5 R; 260/514 G; 260/534 R
[58] Field of Search ...................... 260/247.5 E, 243.7, 260/310 A, 247.2 A; 544/140; 548/363

[56] References Cited

U.S. PATENT DOCUMENTS

| | | | |
|---|---|---|---|
| 3,178,441 | 4/1965 | Ficken | 260/293.7 |
| 3,221,023 | 11/1965 | Marle et al. | 260/293.7 |
| 3,247,201 | 4/1966 | Marle et al. | 260/293.7 |

FOREIGN PATENT DOCUMENTS

| | | | |
|---|---|---|---|
| 1,944,054 | 5/1970 | Germany | 260/247.2 A |

OTHER PUBLICATIONS

Ilford Ltd., C.A., vol. 68:39630j, 1968.

*Primary Examiner*—James O. Thomas, Jr.
*Assistant Examiner*—Michael Shippen

*Attorney, Agent, or Firm*—Cruzan Alexander; Donald M. Sell; Mark A. Litman

[57] ABSTRACT

3-Pyrazolidinone compounds having a solubility of at least 12 grams/liter in an aqueous medium of pH 9 of the formula:

$$Q-CH_2-\underset{\underset{\underset{R}{N}}{H_2C}}{\overset{H}{C}}-\overset{}{\underset{NH}{C=O}}$$

wherein
R is a mononuclear phenyl group having substituents in the 3, 4, or 5 positions with a total of no more than 4 non-metallic atoms with an atomic number greater than 1 and the total mass of the substituents being less than that of benzene,
Q is an aqueous-solubilizing group of the formula:

$$\underset{R^2}{\overset{R^1}{>}}N-$$

wherein
$R^1$ and $R^2$ are independently a hydrogen, or alkyl group or together with the included nitrogen form a 5 or 6 membered heterocyclic ring composed of carbon, nitrogen and no more than one atom from the group of sulfur and oxygen, the total number of atoms in $R^1$ and $R^2$ having an atomic number greater than 1 being equal to or less than 6.

5 Claims, No Drawings

3-PYRAZOLIDINONE DERIVATIVES

This application is a continuation-in-part of U.S. Application Ser. No. 206,168 filed Dec. 8, 1971, now abandoned, which in turn is a continuation of U.S. Application Ser. No. 853,941 filed Aug. 8, 1969, now abandoned.

This invention relates to 3-pyrazolidinone derivatives and also to the use of these derivatives as developing agents for silver halide photographic emulsions. The invention also relates to 3-pyrazolidinimine intermediates for use in the preparation of the 3-pyrazolidinone derivatives and unsaturated organic compounds useful as intermediates in the preparation of both the 3-pyrazolidinones and 3-pyrazolidinimines.

1-Phenyl-3-pyrazolidinone is a good developing agent on its own, but it becomes outstandingly good when it is used in combination with large amounts of other cheaper developing agents such as hydroquinone, since together the two agents are far more efficient than would be expected from a simple addition of their properties. This appears to be the case because the 1-phenyl-3-pyrazolidinone is used over and over again and only finally becomes exhausted once all other chemicals in the developer are also exhausted.

Although 1-phenyl-3-pyrazolidinone is an excellent developing agent its use does have a number of practical disadvantages. One of these is its instability in alkaline solutions with a pH above 9. This means it is not a very suitable developer in high activity liquid developers. Another disadvantage is its relatively low solubility in the developer solutions which rather limits the concentration in which the concentrated developer solutions are sold, and normally customers prefer to buy a concentrated solution which they can easily bring to the correct strength by dilution rather than a solid which has to be dissolved.

So far any attempt to improve the stability or solubility of 3-pyrazolidinone developing agents has been at the expense of one or more of the desirable properties of the developing agent such as its developing activity.

It is an object of the invention, therefore, to provide 3-pyrazolidinone developing agents which have desirable developing properties which are as good as those of 1-phenyl-3-pyrazolidinone, or only slightly worse, but which have a much better stability in highly alkaline solutions and/or are more soluble in the developer solutions.

It has been found that 3-pyrazolidinones having a solubility of at least 12 grams/liter and having the structural formula:

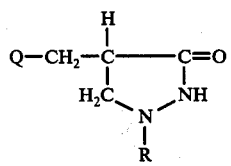

wherein R is a mononuclear phenyl group having substituents in the 3,4, or 5 positions with a total of no more than 4 non-metallic atoms with an atomic number greater than 1 and the total mass of the substituents being less than that of benzene, Q is an aqueous-solubilizing group of the formula:

wherein $R^1$ and $R^2$ are independently a hydrogen, or alkyl group or together with the included nitrogen form a 5 or 6 membered heterocyclic ring composed of carbon, nitrogen and no more than one atom from the group of sulfur and oxygen, the total number of atoms in $R^1$ and $R^2$ having an atomic number greater than 1 being equal to or less than 6 are useful according to the practice of this invention. It has been found that the most useful substituents on the phenyl group R are those in which the linkage to the phenyl ring is not made through an oxygen, sulfur, or nitrogen atom.

These 3-pyrazolidinone compounds make good developing agents for photographic silver halide emulsions and they are considerably more soluble and/or stable in highly alkaline solutions than 1-phenyl-3-pyrazolidinone.

While the compounds of the invention are themselves developing agents, they are preferably used with one or more other developing agents such as for example hydroquinone since, like 1-phenyl-3-pyrazolidinone, such a combination gives an excellent developer which can be re-used many times before exhaustion. Another very useful developer combination which is particularly suited for use in the development of color photographic materials is a compound of the invention with N,N'-diethyl-paraphenylene-diamine or other color developer.

Suitable rings represented by the group $R^1$ and $R^2$ together with the nitrogen atom are morpholino and piperidino rings.

When $R^1$ and $R^2$ represent a substituted alkyl group, suitable substituents include, for example, hydroxy and tertiary amine groups since these confer on the compounds increased solubility in water or other developer solvents such as, for example, alcohols.

When R represents a substituted aryl group suitable substituents include, for example, alkyl and alkoxy groups and halogen atoms.

The 3-pyrazolidinone compounds of the invention can be made in a number of different ways.

One method of preparation involves reacting an ester having the general formula:

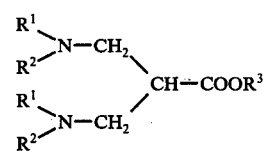

in which $R^1$ and $R^2$ are as defined above and $R^3$ represents a hydrogen atom or an alkyl group, with the substituted hydrazine having the general formula:

RNH.NH$_2$ in which R is as defined above. The reaction can be effected by heating a mixture of the two reactants in solution.

Another method involves the hydrolysis of a 3-pyrazolidinimine; for example, by boiling the imine in solution in an aqueous mildly acidic solution. Therefore according to another aspect of the invention there are provided 3-pyrazolidinimine intermediates of the general formula:

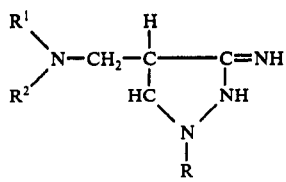

wherein R is a mononuclear phenyl group having substituents in the 3, 4, or 5 positions with a total of no more than 4 non-metallic atoms with an atomic number greater than 1 and the total mass of the substituents being less than that of benzene,
wherein $R^1$ and $R^2$ are independently a hydrogen, or alkyl group or together with the included nitrogen form a 5 or 6 membered heterocyclic ring composed of carbon, nitrogen and no more than one atom from the group of sulfur and oxygen, the total number of atoms in $R^1$ and $R^2$ having an atomic number greater than 1 being equal to or less than 6.

The 3-pyrazolidinone compounds of the invention can further be prepared by reacting an unsaturated organic compound containing an aminomethylene group and which has the general formula:

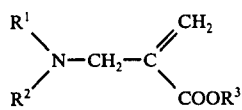

in which $R^1$, $R^2$ and $R^3$ are as defined above, with a substituted hydrazine, such as phenylhydrazine, having the general formula:

in which R is as defined above. The reaction can be effected by heating the reactants together in solution.

In addition to being able to prepare the 3-pyrazolidone compounds of the invention from these unsaturated organic compounds, the 3-pyrazolidinimine intermediates described above can also be prepared by reacting one of these unsaturated organic compounds containing an aminomethylene group with a substituted hydrazine, such as phenyl-hydrazine, having the general formula:

in which R is as defined above. This reaction can, for example, be effected by boiling the reactants together in solution in a solvent such as ethanol.

The invention in another aspect relates to the preparation of these unsaturated organic compounds. Therefore according to this aspect of the invention there is provided a process for the preparation of unsaturated organic compounds containing an amino-methylene group and having the general formula:

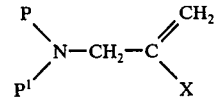

in which P and $P^1$ are independently a hydrogen, or alkyl group or together with the included nitrogen form a 5 or 6 membered heterocyclic ring composed of carbon, nitrogen and no more than one atom from the group of sulfur and oxygen, the total number of atoms in P and $P^1$ having an atomic number greater than 1 being equal to or less than 6, and X represents an electron withdrawing group, comprising reacting under alkaline conditions an amine having the general formula:

in which P and $P^1$ are as above, formaldehyde, and a compound containing an active methylene group adjacent to a carboxyl group and having the general formula:

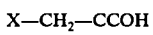

in which X is as defined above.

Although we are not certain of this, we believe that this process proceeds at least in part by way of an intermediate stage in which a methane bis-amino compound is formed which then reacts with the compound having the general formula: $X—CH_2—COOH$. In any case, the final unsaturated organic compound can be prepared by reacting a methane bis-amino compound and the compound having the general formula: $X—CH_2—COOH$ and therefore according to a further feature there is provided a process for the preparation of these unsaturated organic compounds containing an aminomethylene group and having the general formula:

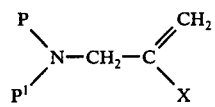

in which P and $P^1$ and X are as defined above, comprising mixing a methane bis-amino compound having the general formula:

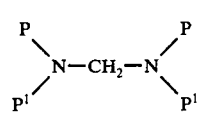

with a compound containing an active methylene group adjacent to a carboxyl group and having the general formula:

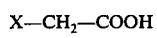

in which X is as defined above.

As noted above these unsaturated compounds are useful intermediates in the preparation of 3-pyrazolidinone compounds and 3-pyrazolidinimine compounds described above, in which case P and $P^1$ can then represent the same groupings as R and $R^1$. In addition, because these unsaturated compounds contain a vinyl linkage, they can be polymerised to give homopolymers and copolymers when polymerised with one or more other copolymerisable monomers.

The group represented by X must have the effect of withdrawing electrons and suitable groupings are, for example those having the formulae: —COOH, —COOP" and —CN in which P² represents an alkyl, aryl or aralkyl group.

In the preparation of these unsaturated compounds one can use the formaldehyde either as such or it can be added to the reaction mixture in the form of its precurser paraformaldehyde.

The preparation of these unsaturated compounds is preferably effected in an aqueous reaction medium.

In the case of unsaturated compounds where X represents a carboxyl group (—COOH), one can convert them to the corresponding compounds where X represents the ester group —COOP² by treating the unsaturated compound where X represents —COOH with an alcohol in the presence of a strong acid such as sulphuric acid.

The invention will now be illustrated by the following Examples.

Examples 1 to 10 illustrate the preparation of the unsaturated organic intermediate compounds.

EXAMPLE 1

2-Dimethylaminomethylacrylic acid.

Formaldehyde solution (150 ml of 40% solution) was added with stirring to a solution of dimethylamine (218g of 26% solution) and malonic acid (104g) in water (250 ml). The reaction temperature was kept at 20° C during the addition and for a further 2 hours. The solution was then heated on a steam bath for 2 hours and the water was removed under reduced pressure to give a pale yellow syrup which was dried further by azeotropic distillation with benzene.

The produce was recrystallised from acetone to give colourless crystals which were dried under vacuum over phosphorous pentoxide for four days. The yield was 92g or 71%.

Analysis: $C_6H_{11}NO_2$ requires: N, 10.85%, Found: N, 10.70%.

EXAMPLE 2

2-Piperidinomethylacrylonitrile

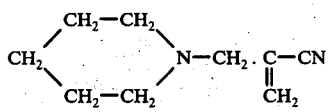

Formaldehyde (75 ml of 40% solution) was added to a stirred solution of cyanacetic acid (43g) and piperidine (85g) in water at 15° C. The solution was stirred for 1 hour at room temperature and then boiled under reflux for 2 hours. On cooling the reaction mixture separated into two layers, the top layer was separated and distilled to give a colourless oil, boiling point 117°–118° C 0.5mm.

Analysis: $C_9H_{14}N_2$ requires: C 71.96%, H 9.37%, N 18.63%, Found: C 71.6%, H 10.4%, N 18.55%.

EXAMPLE 3

2-Dimethylaminomethylacrylonitrile

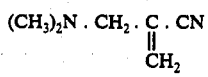

Formaldehyde (75g of 40% solution) was added to a stirred solution of cyanacetic acid (43g) and dimethylamine (173g of 26% solution) in water (250 ml) at 15° C. After stirring for one hour the solution was boiled under reflux for 1 hours. The reaction mixture separated into two layers on cooling and the top layer was separated and distilled giving 2-dimethylaminomethylacrylonitrile (boiling point 40°-45° C/0.5mm) and a higher boiling by-product.

Analysis: $C_6H_{10}N_2$ requires: C 65.45%, H 9.15%, N 25.45% Found: C 65.1%, H 8.8%, N 25.3%.

EXAMPLE 4

Ethyl 2-dimethylaminomethylacrylate

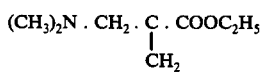

Formaldehyde (60 ml of 40% solution) was added to a stirred solution of potassium ethyl malonate (34g) and dimethylamine (40 ml of 26% solution) in water (100 ml) at 15° C. The solution was stirred at laboratory temperature for one hour and then boiled under reflux for one hour. After cooling the solution was extracted with ether and the ether was evaporated to leave the product as a yellow oil. This was distilled to give a clear oil (boiling point 84° C/20 mm).

Analysis: $C_8H_{15}NO_2$ requires: C, 16.1%, H, 9.62%, N, 8.91%, Found: C, 60.7%, H, 10.15%, N, 8.93%.

EXAMPLE 5

Ethyl 2-dimethylaminomethylacrylate

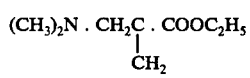

A solution of the 2-dimethylaminomethylacrylic acid (35 g) compound prepared as in Example 1 in ethanol (350 ml) and concentrated sulphuric acid (60 ml) were boiled under reflux for three hours. The solution was evaporated to half volume and poured into water (1 liter). The aqueous solution was neutralised by the addition of solid sodium carbonate and extracted with ether. Evaporation of the ether solution gave a pale brown oil which was distilled to give a colourless oil (boiling point 84° C/20 mm). The product was identical with that obtained in Example 4.

EXAMPLE 6

2-Dimethylaminomethylacrylic acid.

Aqueous formaldehyde (162 ml of 37% solution) was slowly added to a solution of malonic acid (104g) and dimethylamine (350 ml 26% of aqueous solution) in water (150 ml) at 15° C with stirring. Carbon dioxide was evolved at a rate dependent upon the rate of addition of formaldehyde. The reaction mixture was stirred for 30 minutes at 15° C and then heated on a steam bath for 1 hour to ensure complete decarboxylation. Evaporation of the solvent under reduced pressure gave a yellow syrup, which was dried further by azeotropic distillation with toluene to obtain a pale brown solid. The crude material was recrystallised from acetone and dried in vacuum over phosphorus pentoxide to give colourless cubes of the product (107g, 86%, melting point 115 to 7° C).

Analysis: $C_6H_{10}NO_2$ requires: C, 55.8%, H, 8.6%, N, 10.8%, Found: C, 54.2%, H, 8.5%, N, 10.7%.

EXAMPLE 7

2-Diethylaminomethylacrylic acid

Malonic acid (5.2g) was added in portions to bis-diethylamino-methane (24g), cooled in ice and stirred manually. A violent reaction took place and the mixture became viscous. Evaportion of the excess bis-diethylamino-methane and diethylamine gave a syrup which was repeatedly recrystallised from acetone to give colourless crystals of 2-diethylaminomethylacrylic acid (5.9g, 76% melting point 121 to 3° C).

Analysis: $C_8H_{15}NO_2$ requires: C, 61.1%, H, 9.6%, N, 8.9%, Found: C, 58.4%, H, 10.2%, N, 7.69%.

Other 2-aminomethylacrylic acids were prepared by similar methods and the properties of the resulting products are listed below in Table 1, the amino group Q in the table corresponding to the group Q of the general formula:

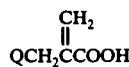

EXAMPLE 8

Ethyl 2-dimethylaminomethylacrylate

Aqueous formaldehyde (161 ml, 37%) was added slowly to a solution of ethyl hydrogen malonate (132g) and dimethylamine (350 ml, 26% aqueous) in water (150 ml) at 15° C. The mixture was stirred at 15° C for 30 minutes, heated slowly to 40° C and stirred for a further 30 minutes. Decarboxylation commenced at 26° C. After cooling, the organic material which had separated as a colourless oil was extracted with ether (3 × 250 ml). The ether extracted was dried over anhydrous sodium sulphate and evaporated at atmospheric pressure. The residue was shown to be a mixture by the appearance of two carbonyl peaks (1740 cm$^{-1}$ and 1720 cm$^{-1}$) in the infrared spectrum. The mixture was distilled under vacuum to give ethyl 2-dimethylaminomethylacrylate (50g, 32% boiling point 34° C/0.7mm; $\nu_{c=o}$ 1722cm$^{-1}$) and ethyl 1,3-bis (dimethylamino) propane-2-carboxylate (87g, 43%, boiling point 58° C/0.8mm; $\nu_{c=o}$ 1740 cm$^{-1}$).

Analysis for ethyl 2-dimethylaminomethylacrylate: $C_8H_{15}NO_2$ requires: C, 61.1%, H, 9.6%, N, 8.9%, Found: C, 60.6%, H, 10.1%, N, 8.8%.

Analysis for ethyl 1,3-bis (dimethylamino) propane-2-carboxylate: $C_{10}H_{22}NO_2$ requires: C, 59.4%, H, 10.9%, N, 13.8%, Found: C, 58.6% H, 11.5%, N, 12.3%.

Other 2-alkylaminomethylacrylic esters were prepared in this way and the properties of the resulting compounds are shown in the following Table 2 in which Q and $Q^1$ in the Table represent the groups in the general formula:

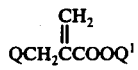

Table 1

| Q | Melting point (° C) | Analysis found (%) | | | required (%) | | | Form of crystals | Recrystallisation solvent used |
|---|---|---|---|---|---|---|---|---|---|
| | | C | H | N | C | H | N | | |
| amino | 145-151 | 45.4 | 7.7 | 15.4 | 47.5 | 7.0 | 13.9 | cubes | acetone/methanol |
| methylamino | 137-146 | 50.7 | 7.4 | 11.4 | 52.2 | 7.9 | 12.1 | cubes | acetone/methanol |
| dimethylamino | 115-7 | 55.2 | 8.5 | 10.7 | 55.8 | 8.6 | 10.8 | cubes | acetone |
| diethylamino | 121-3 | 58.4 | 10.2 | 9.6 | 61.1 | 9.6 | 8.9 | plates | acetone |
| dicyclohexylamino | 147-8 | 72.6 | 10.0 | 5.0 | 72.4 | 10.3 | 5.3 | plates | acetone |
| 1-piperidino | 144-5 | 63.3 | 8.9 | 8.1 | 63.9 | 8.9 | 8.3 | plates | acetone |
| 1-morpholino | 114-5 | 55.1 | 7.6 | 8.2 | 56.1 | 7.6 | 8.2 | plats | acetone |

Table 2

| Q | $Q^1$ | Boiling point (° C) | at pressure (mm) | Analysis found % | | | required % | | |
|---|---|---|---|---|---|---|---|---|---|
| | | | | C | H | N | C | H | N |
| Methylamino | $C_2H_5$ | 106 | 2.0 | 56.8 | 10.5 | 8.9 | 58.7 | 9.2 | 9.8 |
| Dimethylamino | $CH_3$ | 77 | 20.0 | 57.9 | 8.9 | 9.6 | 58.7 | 9.2 | 9.8 |
| Dimethylamino | $C_2H_5$ | 84 | 20.0 | 60.6 | 10.1 | 8.9 | 61.1 | 9.6 | 8.9 |
| Diethylamino | $CH_3$ | 94 | 15.0 | 59.0 | 9.6 | 7.5 | 63.1 | 10.0 | 8.2 |
| Diethylamino | $C_2H_5$ | 56 | 2.0 | 64.0 | 9.9 | 7.7 | 64.8 | 10.3 | 7.6 |
| 1-Piperidino | $CH_3$ | 80 | 2.0 | 62.8 | 8.8 | 7.3 | 65.5 | 9.3 | 7.6 |
| 1-Piperidino | $C_2H_5$ | 117 | 15.0 | 65.9 | 9.6 | 7.0 | 66.9 | 9.7 | 7.1 |
| 1-Piperidino | $CH_3CH-CH_3$ | 94 | 1.0 | 66.6 | 10.1 | 5.9 | 68.2 | 10.0 | 6.2 |
| 1-Piperidino | $nC_4H_9$ | 102 | 1.0 | 67.5 | 10.3 | 5.4 | 69.3 | 10.3 | 6.2 |

Table 2-continued

| Q | $Q^1$ | Boiling point (° C) | at pressure (mm) | Analysis found % C | H | N | required % C | H | N |
| --- | --- | --- | --- | --- | --- | --- | --- | --- | --- |
| 1-Morpholino | $C_2H_5$ | 94 | 1.0 | 60.3 | 8.8 | 7.1 | 60.3 | 8.6 | 7.0 |

EXAMPLE 9

2-Dimethylaminomethylacrylonitrile

Aqueous formaldehyde (162 ml, 37%) was added slowly to a solution of cyanacetic acid (85g) and dimethylamine (350 ml, 26% aqueous). The solution was stirred at 15° C during the addition and then at 40° C for a further 30 minutes. Carbon dioxide evolution commenced at 31° C, the rate of evolution increasing with rising temperature. The solution was extracted with ether (3 × 250 ml), after drying over anhydrous sodium sulphate, the solvent was evaporated at atmospheric pressure to give an oil. The infrared spectrum of the oil showed two nitrile peaks (2240cm$^{-1}$ and 2220cm$^{-1}$) indicating the pressure of two compounds. Distillation of the mixture gave 2-dimethylaminomethylacrylonitrile (25g, 23%, boiling point 43° C/1.0mm) and 1,3-bis(dimethylamino) propane-2-nitrile (43g, 31% boiling point 57° C/0.8mm).

Analysis for 2-dimethylaminomethylacrylonitrile: $C_6H_{10}N_2$ requires: C, 65.4%, H, 9.2%, N, 25.4%, Found: C, 65.2%, H, 9.2%, N, 25.4%.

Analysis for 1,3-bis(dimethylamino) propane-2-nitrile: $C_8H_{17}N_3$ requires: C, 61.9%, H, 11.0%, N, 27.1%, Found: C, 62.3%, H, 10.8%, N, 27.1%.

Other 2-alkylaminomethylacrylonitriles were prepared in the same way and their properties are listed in the following Table 3 in which the amino group Q represents the group Q in the following general formula:

$$QCH_2\overset{CH_2}{\underset{\|}{C}}CN$$

Table 3

| Q | Boiling Point (° C) | at pressure (mm) | Analysis found (%) C | H | N | required (%) C | H | N |
| --- | --- | --- | --- | --- | --- | --- | --- | --- |
| Dimethylamino | 56 | 10.0 | 65.2 | 9.2 | 25.4 | 65.4 | 9.2 | 25.4 |
| Diethylamino | 40 | 1.0 | 69.1 | 10.4 | 20.3 | 69.5 | 10.2 | 20.3 |
| 1-Piperidino | 117 | 0.5 | 71.6 | 9.8 | 18.6 | 71.9 | 9.4 | 18.7 |

EXAMPLE 10

Ethyl-2-dimethylaminomethylacrylate

A solution of 2-dimethylaminomethylacrylic acid (129g) in concentrated sulphuric acid (105 ml, 98%) and ethanol (500 ml) was boiled under reflux for 3 hours. After evaporating to half volume and pouring the residue into water (1 liter), anhydrous sodium carbonate (212g) was added and the solution was allowed to stand for 3 hours, when it gave a neutral reaction. The aqueous mixture was extracted with ether (3 × 250 ml), after drying over anhydrous sodium sulphate, the ether extract was evaporated at atmospheric pressure. The residual pale yellow oil was distilled under reduced pressure to give ethyl 2-dimethylaminomethylacrylate (86g, 55% boiling point 84° C/20 mm).

Analysis: Calculated for $C_8H_{15}NO_2$: C, 61.1%, H, 9.6%, N, 8.9%, Found: C, 60.7%, H, 10.1%, N, 8.9%.

The following Examples 11 to 13 illustrate the preparation of the 3-pyrazolidinimine intermediate compounds.

EXAMPLE 11

4-Piperidinomethyl-1-phenylpyrazolidin-3-imine

α-Piperidinomethylacrylonitrile (17g) and phenylhydrazine (10.8g) were added to a solution of sodium ethoxide (2.3g sodium) in ethanol (200 ml). The resulting solution was boiled under reflux for 2 hours and a solid precipitate formed during the reaction. Dilute hydrochloric acid (50 ml of 2N) was added to the reaction mixture and the solution was evaporated to dryness. The solid residue was extracted with dry ethanol and the product crystallised from the ethanol as colourless plates (melting point 186-7° C).

Analysis: $C_{15}H_{22}N_4$ requires: C, 69.7%, H, 8.6%, N, 21.7%, Found: C, 69.6%, H, 8.8%, N, 21.6%.

EXAMPLE 12

4-Morpholinomethyl-1-phenylpyrazolidin-3-imine

α-Morpholinomethylacrylonitrile (54g) and phenylhydrazine (37g) were boiled under reflux with a solution of sodium ethoxide (7.5g sodium) in ethanol (250 ml) for two hours. A solid product was formed during the reaction. Dilute hydrochloric acid (160 ml 2N) was added and the solution was evaporated to dryness. The solid residue was extracted with dry ethanol and the product crystallised from the ethanol as colourless plates (melting point 204-5° C).

Analysis: $C_{14}H_{19}N_3O_2$ requires: C, 64.61%, H, 7.76%, N, 21.52%, Found: C, 64.68%, H, 7.6%, N, 21.68%.

EXAMPLE 13

4-Dimethylaminomethyl-1-phenylpyrazolidin-3-imine.

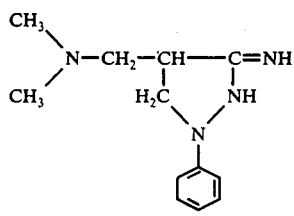

2-Dimethylaminomethylacrylonitrile (11.0g) was added in one portion to a solution of phenylhydrazine (10.8g) and sodium ethoxide (2.3g sodium) in ethanol (100 ml). The product was rapidly oxidised in alkaline solution to a deep purple material; contact with oxygen was prevented by vigorous boiling of the solvent during 1½ hours reflux. After cooling, the sodium ethoxide was neutralised with sulphuric acid (50 ml 2N) and the mixture was extracted with chloroform (3 × 100 ml). Evaporation of the solvent gave a brown solid (17.8g) which was recrystallised from petroleum ether (boiling point 80°-100° C; 300 ml) to yield colourless plates (16.4g, 75%, melting point 117°-8° C).

Analysis: $C_{12}H_{18}N_4$ requires: C, 66.0%, H, 8.3%, N, 25.7%, Found: C, 65.8%, H, 8.2%, N, 25.79%.

The 3-pyrazolidinimine compounds prepared in these Examples 11 to 13 are useful intermediates in the preparation of the 3-pyrazolidinone compounds of the invention.

The following Examples 14 to 19 illustrate the preparation of 3-pyrazolidinone compounds according to the invention.

Example 14

4-Morpholinomethyl-1-phenylpyrazolidin-3-one

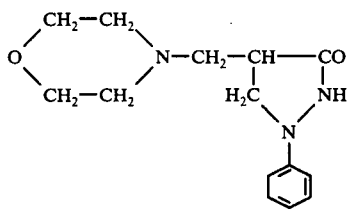

A solution of 4-morpholinomethyl-1-phenylpyrazolidin-3-imine (29g) in dilute hydrochloric acid (120 ml of 2N) was boiled under reflux for 4 hours. The solution was cooled, neutralised with sodium hydroxide and extracted with chloroform. The chloroform extract was dried and evaporated to dryness. The solid residue was recrystallized from petroleum ether (boiling point 100°-120° C) as colourless plates (melting point 143°-144° C).

Analysis: $C_{14}H_{19}N_3O_2$ requires: C, 64.35%, H, 7.33%, N, 16.08%, Found: C, 64.5%, H, 7.4%, N, 16.3%.

EXAMPLE 15

4-Morpholinomethyl-1-phenyl-pyrazolidin-3-one

Ethyl α-morpholinomethylacrylate (10g) was added to a solution of phenylhydrazine (5.4g) and sodium ethoxide (1.15g) of sodium) in ethanol (100 ml) and the mixture was boiled under reflux for 30 minutes. The sodium salt of the product precipitated from the reaction during this time. The suspension was cooled and dilute hydrochloric acid (25 ml of 2N) was added. The solution was evaporated to dryness and the sticky residue was extracted with chloroform. The chloroform solution was evaporated to dryness to give a brown residue. This was recrystallised from petroleum ether (boiling point 100°-120° C) as colourless plates (melting point 143°-4° C).

The product was found to be identical with the product of Example 14.

EXAMPLE 16

4-Dimethylaminomethyl-1-phenylpyrazolidin-3-one

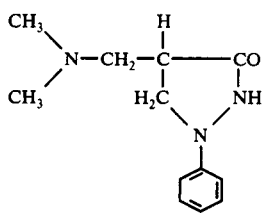

Ethyl-2-dimethylaminomethylacrylate (15.7g) was added in one portion to a boiling mixture of phenylhydrazine (10.8g) and sodium isopropoxide (2.3g of sodium) in isopropanol (100 ml), giving rise to vigorous foaming. The product was rapidly oxidised by air in alkaline solution to give a deep purple material. In order to avoid contact with air the solvent was boiled vigorously under reflux during the subsequent heating. After 10 minutes boiling, the solution was cooled rapidly to 0° C in a flask sealed with a rubber bung. Sulphuric acid (125 ml, 2N) was added and the mixture was extracted with ether (3 × 250 ml). The ether extract was discarded and the aqueous solution was adjusted to a pH of 8 with sodium hydroxide solution (approx. 125 ml, 2N). Extraction of the aqueous mixture with chloroform (3 × 100 ml) gave a pale yellow extract which, after evaporation of the chloroform, gave an oil (18.5g).

The oil crystallised on cooling to a buff solid which was recrystallised from petroleum ether having boiling range of 60° to 80° C (450 ml) to obtain colourless needles of the product, 4-dimethylaminomethyl-1-phenyl-pyrazolidin-3-one (12.4g, 57% melting point 118°-9° C).

Analysis: $C_{12}H_{17}N_3O$ requires: C, 65.7%, H, 7.8%, N, 19.1%, Found: C, 66.5%, H, 7.8%, N, 19.2%.

The hydrogen oxalate salt was prepared by mixing the pyrazolidinone and oxalic acid in acetone solution. This gave a white solid which was recrystallised from ethanol to give colourless crystals of 4-dimethylaminomethyl-1-phenylpyrazolidin-3-one hydrogen oxalate (73% melting point 128°-9° C).

Analysis: $C_{14}H_{19}N_3O_5$ requires: C, 54.5%, H, 6.2%, N, 13.6%, Found: C, 54.5%, H, 6.1%, N, 13.2%.

EXAMPLE 17

4-Dimethylaminomethyl-1-phenylpyrazolidin-3-one

Ethyl-1,3-bis (dimethylamino)-propane-2-carboxylate (20.2g) was added in one portion to a boiling mixture of phenyl-hydrazine (10.8g) and sodium isopropoxide (2.3g of sodium) in isopropanol. The solution was boiled under reflux for 30 minutes and the product (13.6g, 62%) was recovered in a manner similar to that described in Example 16. The product was identified as 4-dimethylaminomethyl-1-phenylpyrazolidin-3-one (melting point 117°-8° C) from its infrared spectrum.

EXAMPLE 18

4-Dimethylaminomethyl-1-p-chlorphenylpyrazolidin-3-one

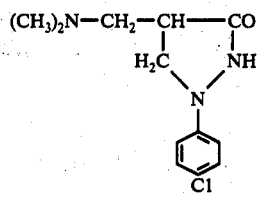

p-Chlorphenylhydrazine (14.5g) was added to a solution of sodium isopropoxide (2.3g of sodium) in dry isopropanol (200 ml). The solution was boiled under reflux and ethyl-2-dimethylaminomethylacrylate (15.7g) was added in one portion. After boiling for 20 minutes, the solution was cooled to 0° C in a stoppered flask. Sulphuric acid (125 ml, 2N) was added and the mixture was extracted with ether (3 × 250 ml). The ether extract was discarded and the aqueous solution was adjusted to a pH of 8 with sodium hydroxide solution (approx 125 ml, 2N). Extraction of the aqueous mixture with chloroform gave a pale yellow extract, which, after evaporation of the chloroform, gave a buff solid. The solid was recrystallised from carbon tetrachloride as colourless needles of 4-dimethylaminomethyl-p-chlorphenylpyrazolidin-3-one (9g, 35%, melting point 107° C).

Analysis: $C_{12}H_{16}ClN_3O$ requires: C, 56.8%, H, 6.4%, N, 16.6% Found: C, 57.1%, H, 6.4%, N, 16.6%.

EXAMPLE 19

4-Piperidinomethyl-1-phenylpyrazolidin-3-one

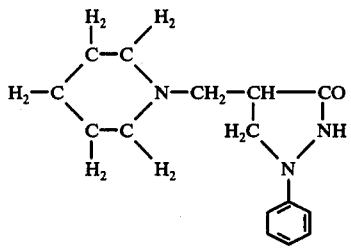

Ethyl 2-piperidinomethylacrylate (19.7g) was added in one portion to a boiling mixture of phenylhydrazine (10.8g) and sodium isopropoxide (2.3g sodium) in isopropanol (100 ml), giving rise to a vigorous foaming. The solution was boiled vigorously under reflux in order to avoid contact of the reaction mixture with air. After boiling for one hour, the solution was cooled rapidly and neutralised with sulphuric acid (50 ml, 2N). The mixture was extracted with chloroform (3 × 100 ml) and the chloroform solution was evaporated to dryness, giving a buff solid.

The solid material was recrystallised from petroleum ether as colourless plates (18.7g, 72%; melting point 134°–5° C).

Analysis: $C_{15}H_{21}N_3O$ requires: C, 69.5%, H, 8.2%, N, 16.3%, Found: C, 69.5%, H, 8.2%, N, 16.3%.

The 3-pyrazolidinone compounds prepared as in these Examples 14 to 19 are excellent photographic emulsion developing agents as illustrated in the following Examples 20 to 22.

EXAMPLE 20

4-Morpholinomethyl-1-phenylpyrazolidin-3-one was examined as a photographic developer in the following solution, termed Solution A:

| | |
|---|---|
| 4-Morpholinomethyl-1-phenylpyrazolidin-3-one | 2.61 g |
| sodium sulphite | 72.0 g |
| sodium carbonate | 48.0 g |
| potassium bromide | 4.0 g |
| hydroquinone | 8.8 g |
| IBT restrainer | 10.0 ml |
| water | to 1000.0 ml. |

Another solution, termed solution B, was prepared which was identical to solution A except that 0.22g of 1-phenylpyrazolidin-3-one was incorporated in place of the 4-morpholinomethyl-1-phenylpyrazolidin-3-one of the invention, this latter solution was used as a standard for comparison.

The following results were achieved when the two solutions were used to develop a commercially available high speed screened medical X-ray film:

| Developer Solution | Fog (base + emulsion) | Relative Speed | Contrast | $D_{(max)}$ | Development time at 70° F (minutes) |
|---|---|---|---|---|---|
| A | 0.19 | 1.97 | 1.89 | 3.12 | 5 |
| B | 0.19 | 1.90 | 2.08 | 3.1 | 5 |

EXAMPLE 21

4-Morpholinomethyl-1-phenylpyrazolidin-3-one was examined for its resistance to oxidation in the same formulation as solution A of Example 20. A control solution, termed solution C, was prepared which was identical to solution B except that it contained 0.22g of 4-methyl-1-phenylpyrazolidin-3-one in place of the 1-phenylpyrazolidin-3-one because the former compound is more stable than the latter. Both solutions were tested for their development of a photographic film when freshly prepared and again after oxygen had been bubbled through them at a rate of 2.5 liters per minute for 6 hours.

The following results were found:

| | Initial Test | | | | |
|---|---|---|---|---|---|
| Developer Solution | Fog (base + emulsion) | Relative Speed | Contrast | $D_{(max)}$ | Development time at 70° F (minutes) |
| A | 0.19 | 1.87 | 2.04 | 3.03 | 5 |
| C | 0.18 | 1.86 | 2.04 | 3.02 | 5 |

| | After Oxidation | | | | |
|---|---|---|---|---|---|
| Developer Solution | Fog (base + emulsion) | Relative Speed | Contrast | $D_{(max)}$ | Development time at 70° F (minutes) |
| A | 0.13 | 1.45 | 1.45 | 3.05 | 5 |
| C | 0.13 | 1.36 | 1.05 | 2.26 | 5 |

EXAMPLE 22

4-Dimethylaminomethyl-1-phenylpyrazolidin-3-one was examined as a photographic developer in a solution, termed solution D, of the same formula as solution A of Example 20 except that it contained 2.19g of 4-dimethylaminomethyl-1-phenylpyrazolidin-3-one in place of the 4-morpholinomethyl-1-phenylpyrazolidin-3-one. This developing solution D was compared with solution B of Example 20 by developed a silver halide emulsion photographic film and the following results were obtained:

| Developer Solution | Fog (base + emulsion) | Relative Speed | Contrast | $D_{(max)}$ | Development time at 70° F (minutes) |
|---|---|---|---|---|---|
| D | 0.15 | 1.76 | 2.09 | 2.90 | 5 |
| B | 0.16 | 1.76 | 2.05 | 2.91 | 5 |

As can be seen from the results of Examples 20 to 22, the compounds of the invention have similar and sometimes better developing properties when compared with prior developers such as 1-phenyl-3-pyrazolidinone and 4-methyl-1-phenylpyrazolidin-3-one. However, the compounds of the invention are more stable to storage in the form of a highly alkaline solution. In addition the compounds of the invention are a great deal more soluble at room temperatures than 1-phenyl-3-pyrazolidinone and 4-methyl-1-phenylpyrazolidin-3-one. Thus, in a developer solution of the composition set out in Example 20, the solubilities of 1-phenylpyrazolidin-3-one and 4-methyl-1-phenylpyrazolidin-3-one are 11.0g/1 and 5.5g/1, respectively, while the compounds of the invention 4-dimethylaminomethyl-1-phenylpyrazolidin-3-one and 4-morpholinomethyl-1-phenylpyrazolidin-3-one have solubilities of 32.0g/1 and 24.0g/1, respectively.

I claim:
1. 4-Morpholinomethyl-1-phenylpyrazolidin-3-one.
2. 4-Dimethylaminomethyl-1-phenylpyrazolidin-3-one.
3. The hydrogen oxalate salt of 4-dimethylaminomethyl-1-phenylpyrazolidin-3-one.
4. 4-Dimethylaminomethyl-1-p-chlorophenyl-pyrazolidin-3-one.
5. 4-Piperidinomethyl-1-phenylpyrazolidin-3-one.

* * * * *